United States Patent
Kitada et al.

(10) Patent No.: US 9,968,768 B2
(45) Date of Patent: May 15, 2018

(54) MEDICAL TUBE, BALLOON CATHETER AND METHOD OF MANUFACTURING MEDICAL TUBE

(71) Applicant: TERUMO KABUSHIKI KAISHA, Shibuya-ku, Tokyo (JP)

(72) Inventors: Noriyuki Kitada, Oyama (JP); Hiroshi Yagi, Fujinomiya (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 337 days.

(21) Appl. No.: 14/661,599

(22) Filed: Mar. 18, 2015

(65) Prior Publication Data
US 2015/0273203 A1   Oct. 1, 2015

(30) Foreign Application Priority Data

Mar. 26, 2014   (JP) .................. 2014-063782

(51) Int. Cl.
*A61M 25/10* (2013.01)
*A61M 39/08* (2006.01)
*A61M 25/00* (2006.01)

(52) U.S. Cl.
CPC ........ *A61M 39/08* (2013.01); *A61M 25/0009* (2013.01); *A61M 25/0043* (2013.01);
(Continued)

(58) Field of Classification Search
CPC .............. A61M 25/0009; A61M 25/10; A61M 25/0045; A61M 25/1034;
(Continued)

(56) References Cited

U.S. PATENT DOCUMENTS 3,282,301 A * 11/1966 Ligon ................. F16L 9/14
                                                  138/175
3,825,036 A *  7/1974 Stent ................. B29C 47/023
                                                  138/174
(Continued)

FOREIGN PATENT DOCUMENTS

JP    S 60222064 A    11/1985
JP    H 09322940 A    12/1997
(Continued)

OTHER PUBLICATIONS

The extended European Search Report dated Aug. 11, 2015, by the European Patent Office in corresponding European Patent Application No. 15159120.3-1506 (8 pgs).
(Continued)

*Primary Examiner* — Nathan R Price
*Assistant Examiner* — Gerald Landry II
(74) *Attorney, Agent, or Firm* — Buchanan Ingersoll & Rooney PC (57) ABSTRACT

A medical tube which is relatively thin in thickness over its entirety while an outer layer and an inner layer are preferably prevented from being separated from each other. A medical tube includes a first layer and a second layer that is provided adjacent to an inner circumferential surface of the first layer. The medical tube also includes a wedge-shaped convex portion that is provided on an outer circumferential surface of the second layer so as to be widened in width radially outward, and a concave portion that is provided on an inner circumferential surface of the first layer, with the convex portion and the concave portion engaging each other.

17 Claims, 8 Drawing Sheets

(52) U.S. Cl.
CPC ..... *A61M 25/0045* (2013.01); *A61M 25/1006* (2013.01); *A61M 2025/0047* (2013.01); *A61M 2025/1093* (2013.01)

(58) Field of Classification Search
CPC .. A61M 2025/0047; A61M 2025/0004; A61M 2025/1086; A61M 2025/1072; A61M 2025/1075
USPC ... 604/96.01, 103.06, 103.08, 509, 523, 524
See application file for complete search history.

(56) References Cited

U.S. PATENT DOCUMENTS

| | | | | |
|---|---|---|---|---|
| 4,261,390 | A * | 4/1981 | Belofsky | B29C 47/021 138/121 |
| 6,165,166 | A * | 12/2000 | Samuelson | A61M 25/0009 604/524 |
| 8,382,709 | B2 * | 2/2013 | Flanagan | A61M 25/1034 604/103.06 |
| 2005/0075626 | A1 * | 4/2005 | Venturelli | A61M 25/0012 604/524 |
| 2006/0085023 | A1 * | 4/2006 | Davies, Jr. | A61M 25/104 606/192 |
| 2008/0262470 | A1 * | 10/2008 | Lee | A61M 25/001 604/509 |
| 2011/0160661 | A1 * | 6/2011 | Elton | A61M 25/10 604/103.06 |
| 2012/0101515 | A1 * | 4/2012 | Barbod | A61M 25/104 606/194 |
| 2013/0190796 | A1 * | 7/2013 | Tilson | A61F 2/2433 606/192 |
| 2013/0192751 | A1 * | 8/2013 | Arai | B29C 65/1635 156/272.6 |
| 2013/0252014 | A1 * | 9/2013 | Sayama | B32B 3/30 428/600 |
| 2015/0012032 | A1 * | 1/2015 | Cox | A61M 25/1018 606/192 |
| 2015/0272732 | A1 * | 10/2015 | Tilson | A61M 25/1002 623/2.11 |

FOREIGN PATENT DOCUMENTS

| | | |
|---|---|---|
| WO | 02/02171 A2 | 1/2002 |
| WO | 03/072177 A1 | 9/2003 |
| WO | 2007/093786 A1 | 8/2007 |

OTHER PUBLICATIONS

Office Action (Notification of Reasons for Refusal) dated Sep. 6, 2017, by the Japanese Patent Office in corresponding Japanese Patent Application No. 2014-063782, and an English Translation of the Office Action. (8 pages).

* cited by examiner

MEDICAL TUBE, BALLOON CATHETER AND METHOD OF MANUFACTURING MEDICAL TUBE

CROSS-REFERENCES TO RELATED APPLICATIONS

This application claims priority to Japanese Application No. 2014-063782 filed on Mar. 26, 2014, the entire content of which is incorporated herein by reference.

TECHNICAL FIELD

The present invention generally relates to a medical tube, a balloon catheter and a method of manufacturing a medical tube.

BACKGROUND DISCUSSION

As a technique of dilating a stenosed portion formed in a blood vessel of a living body, there are widely known so-called percutaneous transluminal angioplasty (PTA) and percutaneous transluminal coronary angioplasty (PTCA) performed by using a balloon catheter.

In the technique using a balloon catheter, a guide wire is first inserted to a stenosed portion. Subsequently, the balloon catheter is caused to creep along the guide wire so that the balloon catheter is thrust into the stenosed portion in its entirety. Then, a balloon is inserted to the stenosed portion. Thereafter, the balloon is filled with a dilation fluid, and the balloon is dilated by increasing a pressure inside the balloon. Then, the stenosed portion is widened, thereby restoring blood flow.

Such a balloon catheter has an inner tube shaft as a medical tube in which the guide wire is inserted through an inner circumference, and an outer circumference of the shaft on a distal side is heat-welded with the balloon. It is preferable to form an inner layer of the inner tube shaft with high density polyethylene (HDPE) having low friction resistance against the guide wire in a view point of insertion properties of the guide wire. It is preferable to form an outer layer of the inner tube shaft with polyamide in a view point of flexibility of the balloon catheter and heat-welding properties with respect to the balloon.

However, in general, a material such as HDPE having low friction resistance against the guide wire and a material such as polyamide that exhibits excellent flexibility and heat-welding properties have poor bonding properties with respect to each other. Therefore when the inner tube shaft is configured to have a concentric double-layered structure, there may be an occurrence of separation between two layers due to relatively low stress (bending, butting, and pressurizing of the balloon) loaded thereon.

In this regard, for example, U.S. Pat. No. 6,165,166 discloses a flexible tube in which an intermediate joint layer is provided between the outer layer and the inner layer. According to the flexible tube, since the intermediate joint layer has bonding properties with respect to the outer layer and the inner layer, the outer layer and the inner layer are indirectly joined. Thus, the outer layer and the inner layer can be prevented from being separated from each other.

SUMMARY

However, in the flexible tube disclosed in U.S. Pat. No. 6,165,166, the thickness of the tube increases by providing an intermediate joint layer between the outer layer and the inner layer, thereby degrading flexibility thereof.

The medical tube disclosed here exhibits excellent flexibility while an outer layer and an inner layer are preferably prevented from being separated from each other. Also disclosed here is a balloon catheter that includes a medical tube and a method of manufacturing a medical tube.

A flexible medical tube according to one aspect of the disclosure here is configured to be positioned in a living body. The medical tube comprises: a first layer possessing an inner circumferential surface; a second layer adjacent to the inner circumferential surface of the first layer, with the second layer possessing an outer circumferential surface; a wedge-shaped convex portion projecting outwardly from the outer circumferential surface of the second layer, with the wedge-shaped convex portion possessing a shape that widens in width in a radially outward direction; a concave portion on the inner circumferential surface of the first layer; and wherein the convex portion is positioned in the concave portion so that the convex portion and the concave portion engage each other.

Another aspect of the disclosures here involves a balloon catheter. The balloon catheter comprises an inner tubular shaft comprised of: a first layer possessing an inner circumferential surface; a second layer adjacent to the inner circumferential surface of the first layer and possessing an outer circumferential surface; a wedge-shaped convex portion projecting outwardly from the outer circumferential surface of the second layer and possessing a shape that widens in width in a radially outward direction; a concave portion on the inner circumferential surface of the first layer; and wherein the convex portion is positioned in the concave portion so that the convex portion and the concave portion engage each other, the inner tubular shaft possesses a distal end. The balloon catheter also comprises: an insertion lumen configured to receive a guide wire; an outer tubular shaft possessing a distal end and including an injection lumen through which a fluid is injectable; and a balloon on the distal end of the inner tubular shaft and the distal end of the outer tubular shaft, wherein the balloon encloses an interior in communication with the injection lumen and expandable outwardly when the fluid injected into the injection lumen flows into the interior of the balloon.

An additional aspect of the disclosure here is a method of manufacturing a flexible medical tube configured to be positioned in a living body. The method of manufacturing comprises coextrusion molding a first layer and a second layer in which the second layer possesses an outer circumferential surface and includes a plurality of wedge-shaped convex portions projecting outwardly from the outer circumferential surface of the second layer and possessing a shape that widens in width in a radially outward direction, and the first layer is arranged on the outer circumferential surface of the second layer and possesses a smooth outer surface.

According to the above-described medical tube, a wedge-shaped convex portion provided on an outer circumferential surface of a second layer, and a concave portion provided on an inner circumferential surface of a first layer mechanically engage each other. Thus, the first layer and the second layer may be preferably prevented from being separated from each other. By having such a configuration, there is no intermediate layer interposed between the first layer and the second layer. Thus, it is possible to provide a medical tube which can be prevented from increasing in thickness and is excellent in flexibility. Therefore, it is possible to provide a medical tube which is excellent in flexibility while the first layer and the second layer are preferably prevented from being separated from each other.

DETAILED DESCRIPTION

Hereinafter, with reference to the drawings, an embodiment of the medical tube, balloon catheter and medical tube manufacturing method, representing one example of the disclosed medical tube, balloon catheter and medical tube manufacturing method disclosed here, will be described. For convenience of description and understanding, dimensional ratios of features shown in the drawings may be exaggerated, thereby being different from the actual dimensional ratios. Here, the embodiment in a case where a medical tube is applied to an inner tubular shaft 10 of a balloon catheter 1 will be described as one example of the medical tube disclosed here. In the descriptions below, an operational grip side of the balloon catheter 1 is referred to as "a proximal side" or "proximal end", and a side to be inserted through into a living body lumen is referred to as "a distal side" or "distal end".

Figure 1:
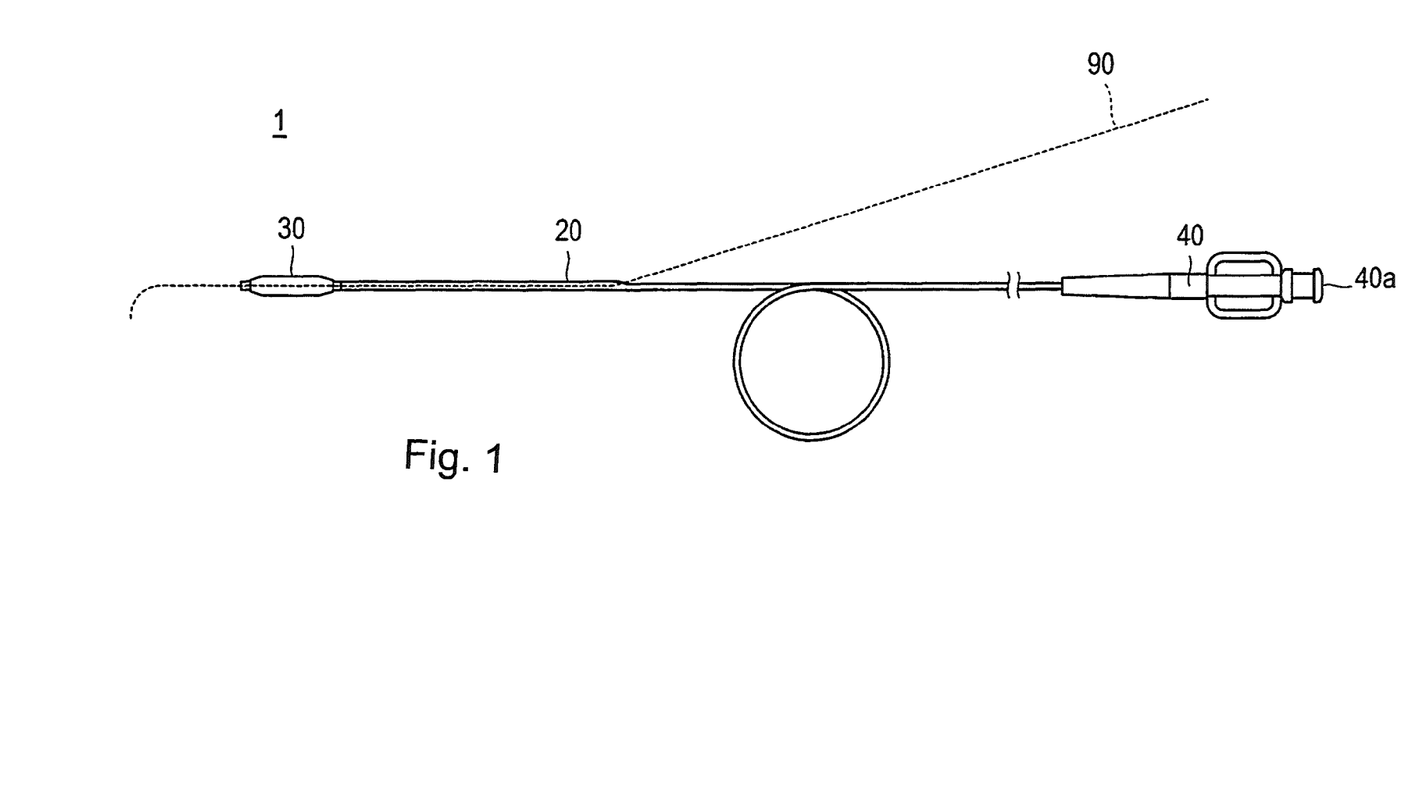
FIG. 1 is a schematic illustration of a balloon catheter according to an embodiment representing one example of the balloon catheter disclosed here.
Figure 2:
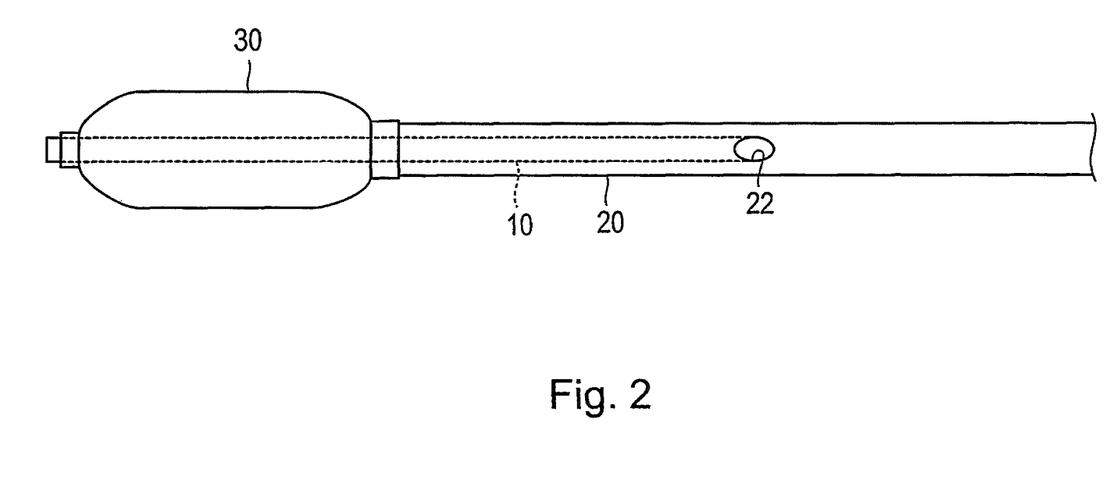
FIG. 2 is a top view illustrating a distal side of the balloon catheter.
Figure 3:
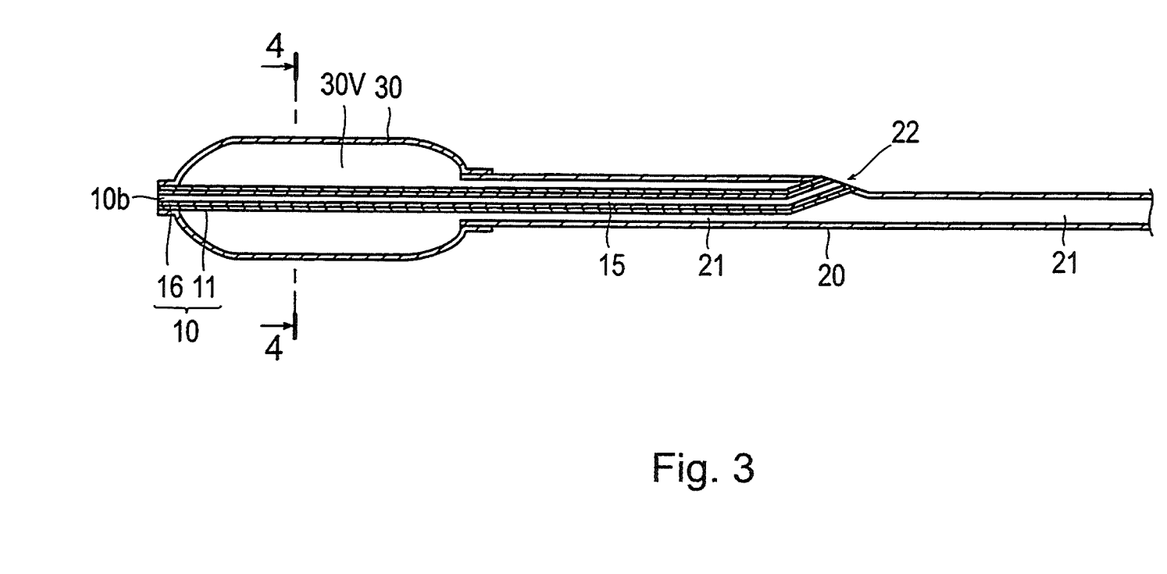
FIG. 3 is a lateral cross-sectional view of FIG. 2.
Figure 4:
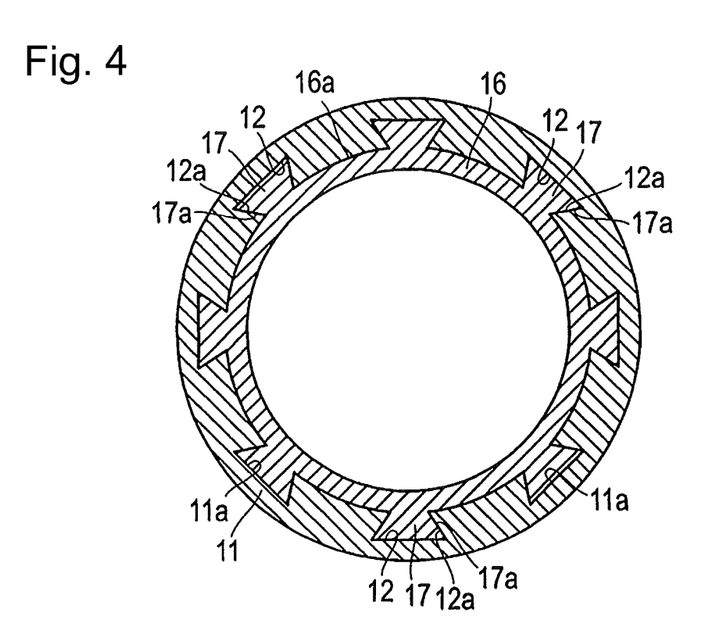
FIG. 4 is a cross-sectional view taken along the section line 4-4 of FIG. 3.
Figure 5:
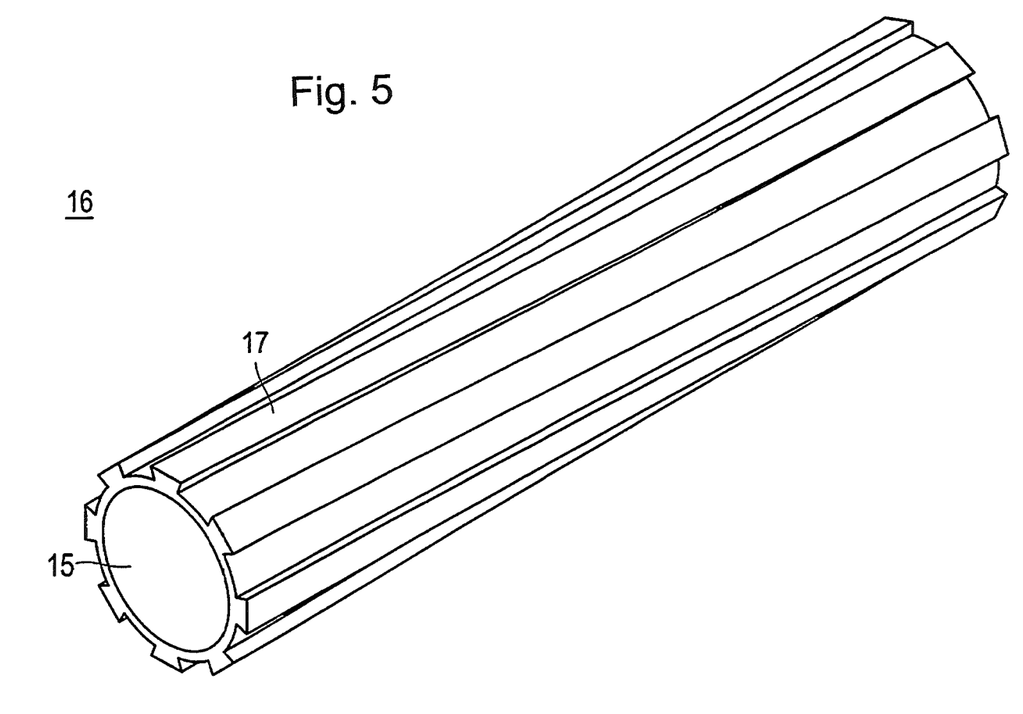
FIG. 5 is a perspective view illustrating an inner layer.

FIG. 1 schematically illustrates the balloon catheter 1 according to an embodiment representing one example of the disclosed balloon catheter. FIG. 2 is a top view illustrating a distal side of the balloon catheter 1. FIG. 3 is a lateral cross-sectional view of FIG. 2. FIG. 4 is a cross-sectional view taken along the section line 4-4 of FIG. 3. FIG. 5 is a perspective view illustrating an inner layer 16. For better understanding, the inner tubular shaft 10 is illustrated in a simplified manner in FIG. 3, and a balloon 30 is not illustrated in FIG. 4.

As illustrated in FIGS. 1 to 5, the balloon catheter 1, which is configured to be positioned in a living body (e.g., a blood vessel of a living body) includes the inner tubular shaft 10, an outer tubular shaft 20, the balloon 30, and a hub 40.

As illustrated in FIG. 3, the inner tubular shaft 10 is a flexible medical tube formed with or comprised of two layers 11 and 16. The two layers 11, 16 include an inner layer 16 and an outer layer 11. An insertion lumen 15 is provided inside the inner layer 16 and is surrounded by an inner circumference of the inner layer 16 of the inner tubular shaft 10. The insertion lumen 15 is configured to receive a guide wire 90 that passes through the insertion lumen 15. The insertion lumen 15 extends inside the balloon 30 and the outer tubular shaft 20 in a transverse direction of FIG. 3. A distal side or distal end of the outer layer 11 of the inner tubular shaft 10 is joined to a distal side or distal end of the balloon 30. Examples of methods for joining the balloon 30 to the outer layer 11 include adhesive or heat-welding. A proximal side or proximal end of the inner tubular shaft 10 is joined to an inner circumference of a guide wire port 22 of the below-described outer tubular shaft 20. Details associated with the configuration of the inner tubular shaft 10 will be described later.

When performing technique procedure using the balloon catheter, the guide wire 90 (a proximal end of the guide wire 90 is inserted into a distal side opening portion 10b (an entrance) of the inner tubular shaft 10, is passed through the insertion lumen 15 provided in the inner circumference of the inner layer 16 of the inner tubular shaft 10 from the distal side to the proximal side, and is led out from the guide wire port 22.

A conventional wire in the medical field can be used as the guide wire 90 to be used together with the balloon catheter 1. For example, the guide wire 90 can be made of a long wire material formed of a metallic material such as a superelastic alloy (a nickel-titanium alloy and a copper-zinc alloy) and stainless steel, or a resin material having relatively high rigidity. The long wire material may be covered with a resin material such as polyvinyl chloride, polyethylene, polypropylene, and an ethylene-propylene copolymer.

As illustrated in FIG. 3, the inner tubular shaft 10 is positioned in the outer tubular shaft 20, with a space between the outer surface of the inner tubular shaft 10 and the inner surface of the outer tubular shaft 20. The outer tubular shaft 20 includes an injection lumen 21 through which a fluid for dilating or outwardly expanding the balloon 30 can be injected, extending in the transverse direction of FIG. 3. A distal side or distal end of the outer tubular shaft 20 is joined to a proximal side or proximal end of the balloon 30. A proximal end of the outer tubular shaft 20 extends to the hub 40, and the injection lumen 21 communicates with an opening portion 40a of the below-described hub 40. The guide wire port 22 which communicates with the insertion lumen 15 and permits insertion of the guide wire 90 into the insertion lumen 15 is provided in the outer tubular shaft 20.

It is preferable that the outer tubular shaft 20 have appropriate flexibility and appropriate rigidity so as to be able to be relatively smoothly inserted into a living body lumen such as a blood vessel. Therefore, for example, the outer tubular shaft 20 may be formed of a polymer material such as polyolefin (for example, polyethylene, polypropylene, polybutene, an ethylene-propylene copolymer, an ethylene-vinyl acetate copolymer, an ionomer, and a mixture of two types or more thereof), polyvinyl chloride, a polyamide, polyamide elastomer, polyurethane, a polyurethane elastomer, polyimide, a fluorocarbon resin, and a mixture thereof. The outer tubular shaft 20 may be formed as a multi-layer tube made of polymer materials composed of two or more types or materials.

The balloon 30 encloses (defines the outer boundary of) an inner space 30V communicating with the injection lumen 21, thereby dilating in response to injection of a fluid into the inner space 30V. The region or volume between the inner surface of the balloon 30 and the outer surface of the inner tubular shaft 10 corresponds to the inner space 30V. Examples of the fluid for dilating the balloon 30 include an X-ray contrast agent, a physiological salt solution, and an electrolyte solution.

It is preferable that a material configuring the balloon 30 have flexibility, for example, a polymer material such as polyolefin, a cross-linked body of polyolefin, polyester, a polyester elastomer, polyvinyl chloride, polyurethane, a polyurethane elastomer, polyphenylene sulfide, polyamide, a polyamide elastomer, and fluorocarbon resin; silicone rubber; and latex rubber. For example, polyester is polyethylene telephthalate. The material forming the balloon 30 is not limited to the aforementioned polymer material alone. For example, it is possible to apply an appropriately laminated film of the aforementioned polymer materials.

The opening portion 40a through which the fluid for dilating the balloon 30 is supplied while an indeflator (a pressure applying device) is interlocked is provided on a proximal end of the hub 40. The fluid supplied from the indeflator is supplied to the inner space 30V of the balloon 30 through the injection lumen 21, thereby dilating or outwardly expanding the balloon 30.

Examples of the material forming the hub 40 include a thermoplastic resin such as polycarbonate, polyamide, polysulfone, polyarylate, and a methacrylate-butylene-styrene copolymer.

Hereinafter, with reference to FIGS. 3 to 5, the configuration of the inner tubular shaft 10 will be described in detail.

In broad terms, as illustrated in FIGS. 3 and 4, the inner tubular shaft 10 includes the outer layer (the first layer) 11 and the inner layer (the second layer) 16. The inner layer 16 is provided adjacent to an inner circumferential surface of the outer layer 11. The inner tubular shaft 10 also includes wedge-shaped convex portions 17 that are provided on and project outwardly from the outer circumferential surface 16a of the inner layer 16. In the illustrated embodiment, the wedge-shaped convex portions 17 possess a shape in cross-section (cross-section perpendicular to the central axis of the tubular shaft 10) that widens in width in a radially outward direction. The inner circumferential surface of the outer layer 11 is provided with concave portions 12 or recesses (grooves) that are configured in a manner the same as the projections 17. That is, the cross-sectional shape (cross-section perpendicular to the central axis of the tubular shaft 10) of the concave portions 12 gradually widens in a radially outward direction. Each of the convex portions 17 is positioned in or engages a respective one of the concave portion 12 as shown in FIG. 4.

The distal end of the outer layer 11 is joined to the distal end of the balloon 30. Therefore, it is preferable that the outer layer 11 have compatibility with respect to the balloon 30. From this view point, examples of materials forming the outer layer 11 include polyamide (PA), a polyamide elastomer, thermoplastic polyurethane (TPU), PET, a polyester elastomer, PEEK, and a mixture thereof.

The guide wire 90 is inserted through the interior or lumen of the inner layer 16. Therefore, it is preferable that the inner layer 16 is a material having relatively low friction resistance with respect to the guide wire 90. From this view point, for example, a material forming the inner layer 16 is HDPE, PTFE, ETFE, FEP, PP, modified PE, modified PP, and a mixture thereof. The inner layer 16 is thus preferably made of a material different from the material forming the outer layer 11.

As described above, the convex portions 17 and the concave portions 12 mechanically engage each other. To be more specific, each first tapered portion 17a widened radially outward in the convex portion 17, and each second tapered portion 12a that narrows radially inward in the concave portion 12 come into surface contact and mechanically engage each other so that the outer layer 11 and the inner layer 16 are joined to each other. The inner tubular shaft 10 having such a configuration is better able to withstand separation of the inner and outer layers 16, 11. For example, with the disclosed construction of the inner tubular shaft 10, the separation load required to separate the outer layer 11 and the inner layer 16 is three times that in a case where the concave portions 12 and the convex portions 17 are not provided, for example.

Eight concave portions 12 and eight convex portions 17 are alternately arranged at equivalent intervals in the circumferential direction. As illustrated in FIG. 5, the convex portions 17 gradually change in position in the circumferential direction along an axial direction. That is, along the axial extent of each of the convex portions 17, the convex portions 17 each extend in a slight helical manner. In this way, the convex portions 17 are not parallel to the central axis of the inner layer 16. Since the concave portions 12 are arranged so as to respectively engage with the convex portions 17 as described above, the concave portions 12 also gradually change in position in the circumferential direction along an axial direction. That is, along the axial extent of each of the concave portions 12, the concave portions 12 each extend in a slight helical manner and so the concave portions 12 are not parallel to the central axis of the inner layer. According to the configuration, it is possible to preferably prevent the outer layer 11 from relatively moving along the axial direction with respect to the inner layer 16.

Subsequently, a method of using the balloon catheter 1 according to the embodiment discussed above by way of example will be described with reference to FIG. 6.

Figure 6A:
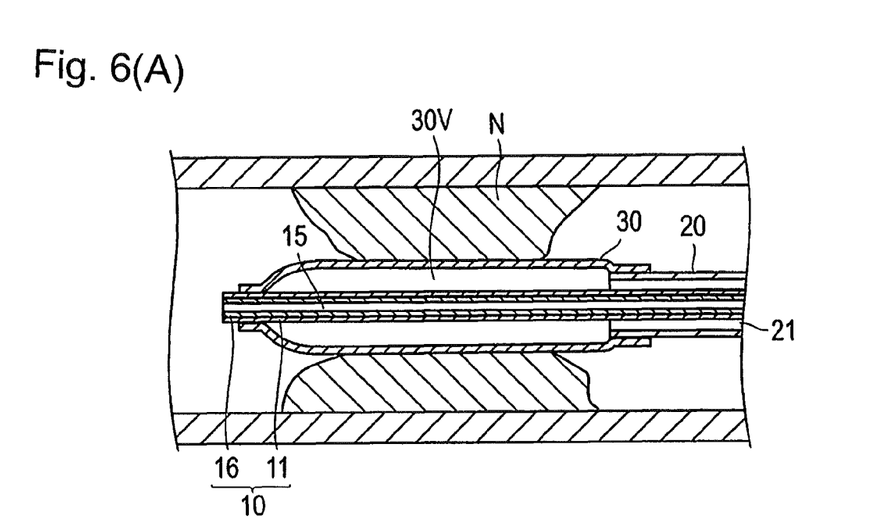
FIG. 6(A) is a diagram illustrating a state before a balloon is dilated.
Figure 6B:
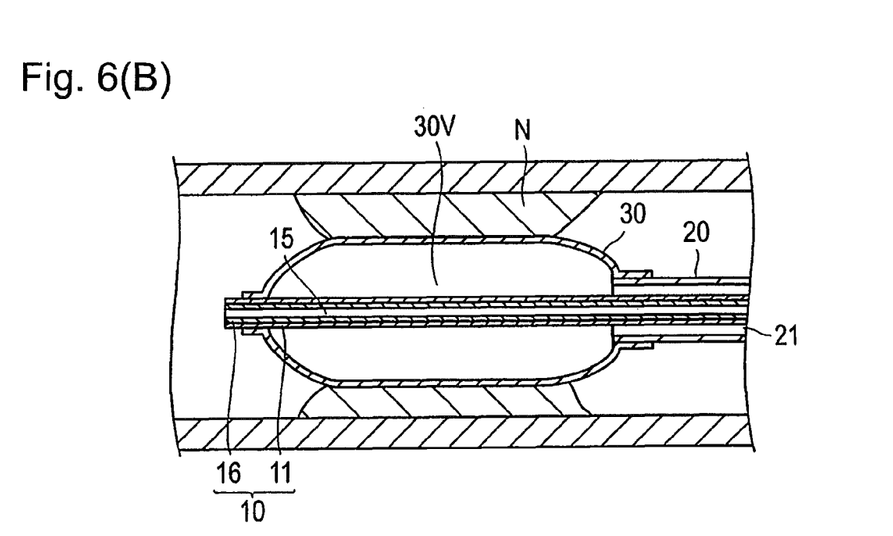
FIG. 6(B) is a diagram illustrating a state after the balloon has been dilated.

FIG. 6(A) is a diagram illustrating a state before the balloon 30 is dilated (i.e., before the balloon is outwardly expanded), and FIG. 6(B) is a diagram illustrating a state after the balloon 30 has been dilated (i.e., after the balloon is outwardly expanded). For better understanding, the guide wire 90 is not illustrated in FIG. 6(A).

When performing the technique of dilating a stenosed portion N by using the balloon catheter 1, the guide wire 90 and the balloon catheter 1 which is in a deflated state are introduced into a living body lumen. In this case, the balloon catheter 1 is caused to creep along the guide wire 90 which is introduced prior to the balloon catheter 1, and the balloon catheter 1 is caused to move until the balloon 30 reaches the inside of the stenosed portion N (refer to FIG. 6(A)). The guide wire 90 is inserted through the insertion lumen 15 of the inner tubular shaft 10.

After the balloon 30 has reached the inside of the stenosed portion N, a fluid is introduced from the opening portion 40a of the hub 40. The balloon 30 is dilated by introducing a fluid into the inner space 30V of the balloon 30 through the injection lumen 21 provided in the inner circumference of the outer tubular shaft 20. As a result, a pressurizing force is applied to the stenosed portion N, thereby widening or expanding the stenosed portion N (refer to FIG. 6(B)). The inner tubular shaft 10 having the above-described configuration is configured so that even though stress loads are applied due to pressurization of the balloon 30, since the concave portion 12 and the convex portion 17 engage each other, it is possible to preferably prevent the outer layer 11 and the inner layer 16 from being separated from each other.

As described above, the inner tubular shaft 10 according to the present embodiment is a flexible medical tube comprised of two layers and includes the outer layer 11 and the inner layer 16, with the inner layer 16 being provided adjacent to the inner circumferential surface of the outer layer 11. The inner tubular shaft 10 also includes the wedge-shaped convex portions 17 that are provided on and project outwardly from the outer circumferential surface 16a of the inner layer 16 in a manner widening in width radially outward, and the concave portions 12 that are provided on the inner circumferential surface 11a of the outer layer 11 so that the convex portions 17 engage the concave portions 12. The convex portions 17 and the concave portions 12 respectively engage each other. Therefore, it is possible to preferably prevent the outer layer 11 and the inner layer 16 from being separated from each other. By having such a configuration, there is no intermediate layer interposed between the outer layer 11 and the inner layer 16. Thus, it is possible to provide the inner tubular shaft 10 without increasing the thickness and while still exhibiting excellent flexibility. Therefore, it is possible to provide the inner tubular shaft 10 which is excellent in flexibility while the outer layer 11 and the inner layer 16 are preferably prevented from being separated from each other.

The illustrated embodiment of the inner tubular shaft 10 representing one example of the disclosed inner tube shaft includes eight convex portions 17 arranged at equivalent intervals in the circumferential direction. Therefore, the outer layer 11 and the inner layer 16 can be equally joined in the circumferential direction, and thus, it is possible to more securely prevent the outer layer 11 and the inner layer 16 from being separated from each other.

The convex portions 17 are configured so as to gradually change in position in the circumferential direction along the axial direction. Therefore, the outer layer 11 can be preferably prevented from relatively moving along the axial extent of the inner layer 16.

As described above, the balloon catheter 1 according to the present embodiment includes the inner tubular shaft 10 that has the above-described configuration and has the insertion lumen 15 through which the guide wire 90 is inserted, the outer tubular shaft 20 that has the injection lumen 21 through which a fluid is injected, and the balloon 30 that is provided on a distal side or distal end of the inner tubular shaft 10 and the outer tubular shaft 20 so as to dilate or outwardly expand in response to injection of the fluid. According to the configuration, it is possible to provide the balloon catheter 1 including the inner tubular shaft 10 which is excellent in flexibility while the outer layer 11 and the inner layer 16 are preferably prevented from being separated from each other.

Hereinafter, modification examples of the above-described embodiment will be illustrated and described.

Modification Example 1

Figure 7:
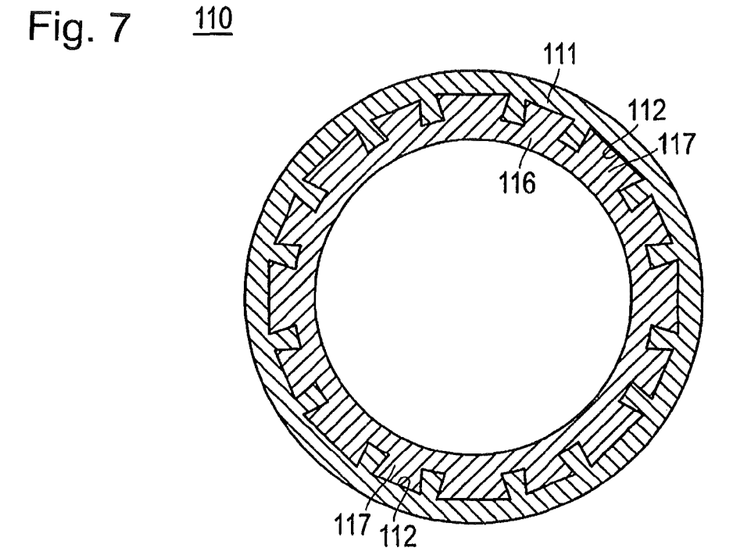
FIG. 7 is a diagram of an inner tubular shaft according to modification example 1 corresponding to FIG. 4.

FIG. 7 is a diagram, similar to FIG. 4, of an inner tubular shaft 110 according to Modification Example 1. In the above-described embodiment, the concave portions 12 and the convex portions 17 are arranged at equivalent intervals in the circumferential direction. However, as illustrated in FIG. 7, concave portions 112 of an outer layer 111 and convex portions 117 of an inner layer 116 may be arranged at unequal intervals in the circumferential direction.

Modification Example 2

Figure 8:
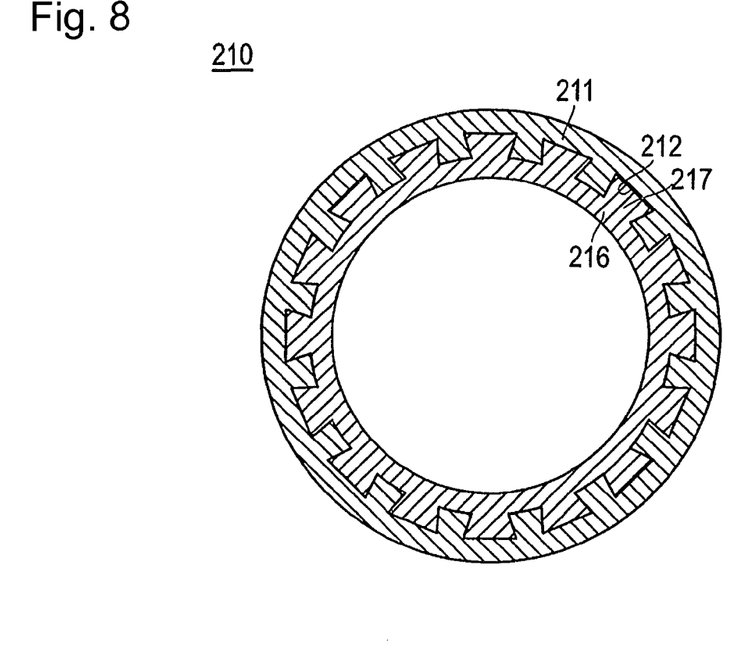
FIG. 8 is a diagram of the inner tubular shaft according to modification example 2 corresponding to FIG. 4.

FIG. 8 is a diagram, similar to FIG. 4, of an inner tubular shaft 210 according to Modification Example 2. In the above-described embodiment, eight concave portions 12 and eight convex portions 17 are respectively arranged at equivalent intervals in the circumferential direction. However, as illustrated in FIG. 8, sixteen concave portions 212 of an outer layer 211 and sixteen convex portions 217 of an inner layer 216 may be arranged at equivalent intervals in the circumferential direction. Moreover, the number of concave and convex portions is not particularly limited as long as the number of concave and convex portions is respectively one or more (i.e., one or more concave portions and one or more convex portions). However, from a viewpoint of adhesion between the outer layer and the inner layer, it is preferable to have four or more concave portions and four or more convex portions.

Hereinafter, as a reference, a method of manufacturing the inner tubular shaft 10 will be described.

Figure 9:
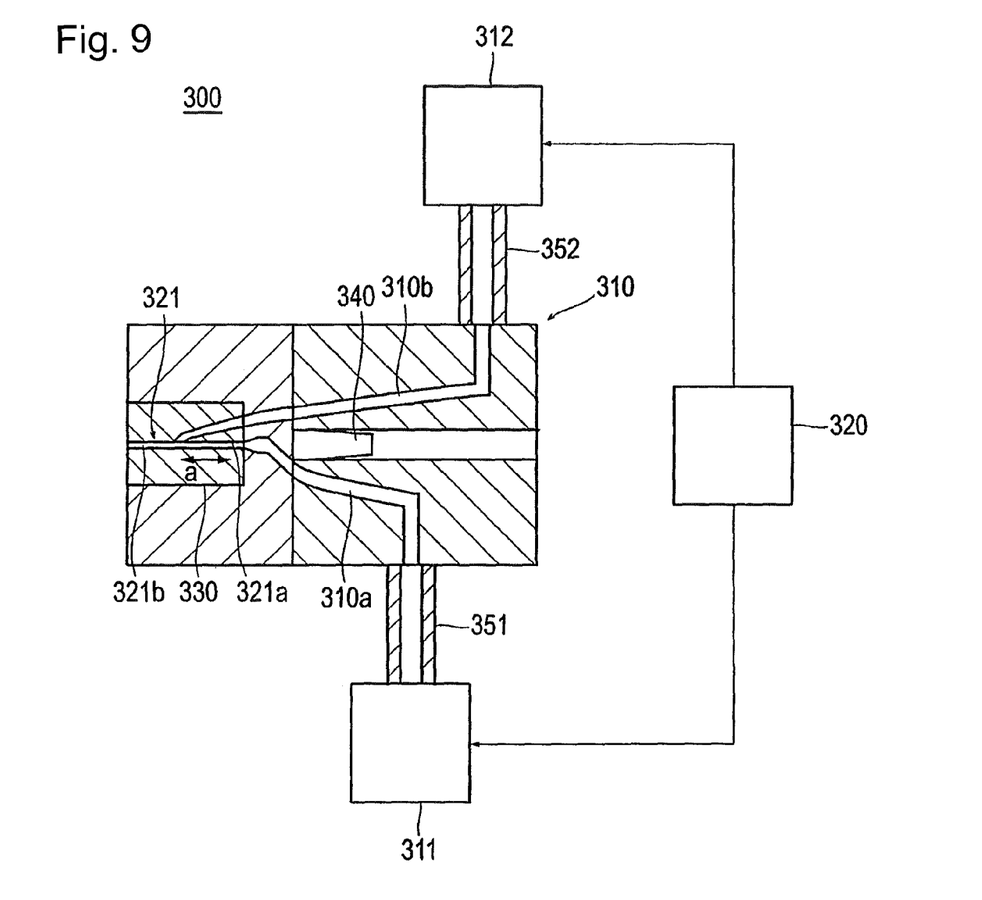
FIG. 9 is a local sectional view simply illustrating an extrusion molding machine used for manufacturing the inner tubular shaft illustrated in FIG. 4.

FIG. 9 illustrates an example of an extrusion molding machine 300 which is used for manufacturing the inner tubular shaft 10.

The extrusion molding machine 300 includes a molding machine main body portion 310, a first extrusion machine 311 which supplies a resin as a material for forming or fabricating the inner layer 16 to the molding machine main body portion 310, a second extrusion machine 312 which supplies a resin as a material for forming or fabricating the outer layer 11 to the molding machine main body portion 310, a control unit 320 which collectively controls operations of each portion of the extrusion molding machine 300, a die 330 which is installed in the molding machine main body portion 310, and a nipple 340 serving as a coupler of a cooling hose connected to cool the molding machine main body portion 310.

As the extrusion machines 311 and 312, for example, it is possible to use conventional machines including a resin insertion port into which a resin as a raw material is inserted, a cylinder into which the resin flows, and a screw which is arranged inside the cylinder and sends a heated and molten resin inside the cylinder to the molding machine main body portion 310. Each of the extrusion machines 311 and 312 are interlocked with the molding machine main body portion 310 through predetermined adapters 351 and 352. A flow path exists inside each of the adapters 351 and 352 through which flows the resin sent by the screw.

The control unit 320 is formed with a conventional microcomputer having a CPU, a RAM, a ROM, and the like. The CPU included in the control unit 320 reads out various programs previously stored in the ROM to the RAM and executes the programs, thereby executing each operation performed by the extrusion molding machine 300. For example, the control unit 320 transmits various signals to the molding machine main body portion 310 and controls the amounts of the resins supplied from each of the extrusion machines 311 and 312 as well as temperatures melting the resin.

Inside the molding machine main body portion 310, a first flow guide path 310a which guides a flow of the resin sent by the first extrusion machine 311 to the die 330 is formed. Similarly, inside the molding machine main body portion 310, a second flow guide path 310b which guides a flow of the resin sent by the second extrusion machine 312 to the die 330 is formed.

Inside the die 330, a resin flow path 321 is formed for molding the resin sent from the extrusion machines 311 and 312 into predetermined shapes and discharging the molded resin from the molding machine main body portion 310.

In the resin flow path 321, a mandrel for forming a lumen (a hollow portion) of the inner layer 16 is arranged throughout the extending direction of the resin flow path 321. In a part (the section indicated by "a" in FIG. 9) of the resin flow path 321 of the die 330, a first molding portion 321a including a molding surface (an inner surface) having a shape which coincides with a cross-sectional shape of an outer surface of the inner layer 16 is formed. Therefore, the resin sent to the resin flow path 321 of the die 330 through the first flow guide path 310a passes through the first molding portion 321a, thereby being molded into the inner layer 16 having a cross-sectional shape in which the lumen and the wedge-shaped convex portions 17 are formed, as illustrated in FIG. 4.

The second flow guide path 310b to which the resin is sent from the second extrusion machine 312 is disposed so as to merge with the resin flow path 321 in a second molding portion 321b which is provided on a downstream side of the flow of the resin relative to a position where the first molding portion 321a is provided. The second molding portion 321b is thus downstream of the position at which the first flow guide path 310a is connected to the die 330. Therefore, the resin sent from the second extrusion machine 312 to the die 330 so as to form the outer layer 11 flows into the resin flow path 321 so as to cover an outer circumference of the inner layer 16 molded in the first molding portion 321a of the resin flow path 321. A molding surface (an inner surface) of the second molding portion 321b is circularly formed so as to coincide with the outer surface of the outer layer 11. Therefore, the resin flowing to the inner layer 16 and the outer circumference thereof via the second molding portion 321b is subjected to coextrusion molding which is accompanied when passing the resin flow path 321 through, thereby being discharged from the die 330 as the inner tubular shaft 10 (a tube) in which the convex portions 17 and the concave portions 12 mechanically engage each other, as illustrated in FIG. 4.

The present invention is not limited to the above-described embodiment and the modification examples, and thus, various changes and modifications can be made within the scope of claims.

For example, in the above-described embodiment, the medical tube is applied to the inner tubular shaft 10 of the balloon catheter 1. However, without being limited thereto, the medical tube can be applied to various other medical tubes such as an introducer sheath, a dilator, a holder tube for a guide wire, and a guiding catheter.

The detailed description above describes a medical tube, a balloon catheter and a method of manufacturing a medical tube. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical tube configured to be positioned in a living body, the medical tube comprising:
   a first layer possessing an inner circumferential surface;
   a second layer adjacent to the inner circumferential surface of the first layer, the second layer possessing an outer circumferential surface;
   a wedge-shaped convex portion projecting outwardly from the outer circumferential surface of the second layer, the wedge-shaped convex portion possessing a shape that widens in width in a radially outward direction;
   a concave portion on the inner circumferential surface of the first layer;
   wherein the wedge-shaped convex portion and the second layer are integrally formed;
   wherein the convex portion is positioned in the concave portion so that the convex portion and the concave portion engage each other; and
   wherein the wedge-shaped convex portion and the second layer are both formed from a same material.

2. The medical tube according to claim 1, wherein a plurality of the convex portions project outwardly from the outer circumferential surface of the second layer and are circumferentially spaced apart from one another, and wherein a plurality of the concave portions are provided on the inner circumferential surface of the first layer and are circumferentially spaced apart from one another, each of the convex portions being positioned in one of the concave portions.

3. The medical tube according to claim 2, wherein each of the convex portions is configured so that a position of the convex portion gradually changes in a circumferential direction along an axial extent of the convex portion.

4. The medical tube according to claim 2, wherein each of the convex portions possesses an axial extent, and each of the convex portions extends in a helical manner about the second layer along the axial extent of the convex portion.

5. The medical tube according to claim 2, wherein the second layer possesses a central axis and each of the convex portions possesses an axial extent, each of the convex portions being non-parallel to the central axis of the second layer along the axial extent of the convex portion.

6. The medical tube according to claim 1, wherein the convex portion is configured so that a position of the convex portion gradually changes in a circumferential direction along an axial extent of the convex portion.

7. The medical tube according to claim 1, wherein the convex portion possesses an axial extent, and the convex portion extends in a helical manner about the second layer along the axial extent of the convex portion.

8. The medical tube according to claim 1, wherein the second layer possesses a central axis and the convex portion possesses an axial extent, the convex portion being non-parallel to the central axis of the second layer along the axial extent of the convex portion.

9. The medical tube according to claim 1, wherein a plurality of the convex portions project outwardly from the outer circumferential surface of the second layer and are circumferentially spaced apart from one another, and wherein a plurality of the concave portions are provided on the inner circumferential surface of the first layer and are circumferentially spaced apart from one another, each of the convex portions being positioned in one of the concave portions, the plurality of the convex portions being equal in total number to the total number of the concave portions.

10. The medical tube according to claim 1, wherein a plurality of the convex portions project outwardly from the outer circumferential surface of the second layer and are circumferentially spaced apart from one another by a circumferential spacing, the circumferential spacing between at least a first and a second immediately circumferentially adjacent convex portions being different.

11. A balloon catheter, comprising:
   an inner tubular shaft comprised of: a first layer possessing an inner circumferential surface; a second layer adjacent to the inner circumferential surface of the first layer and possessing an outer circumferential surface; a wedge-shaped convex portion projecting outwardly from the outer circumferential surface of the second layer and possessing a shape that widens in width in a radially outward direction; a concave portion on the inner circumferential surface of the first layer; wherein the wedge-shaped convex portion and the second layer are integrally formed; and wherein the convex portion is positioned in the concave portion so that the convex portion and the concave portion engage each other, the inner tubular shaft possesses a distal end;

an insertion lumen configured to receive a guide wire;

an outer tubular shaft possessing a distal end and including an injection lumen through which a fluid is injectable;

a balloon on the distal end of the inner tubular shaft and the distal end of the outer tubular shaft, the balloon enclosing an interior in communication with the injection lumen and expandable outwardly when the fluid injected into the injection lumen flows into the interior of the balloon; and wherein the wedge-shaped convex portion and the second layer are both formed from a same material.

12. The balloon catheter according to claim 11, wherein the inner tubular shaft surrounds the insertion lumen.

13. The balloon catheter according to claim 11, wherein the convex portion is configured so that a position of the convex portion gradually changes in a circumferential direction along an axial extent of the convex portion.

14. The balloon catheter according to claim 11, wherein the convex portion possesses an axial extent, and the convex portion extends in a helical manner about the second layer along the axial extent of the convex portion.

15. The balloon catheter according to claim 11, wherein the second layer possesses a central axis and the convex portion possesses an axial extent, the convex portion being non-parallel to the central axis of the second layer along the axial extent of the convex portion.

16. The balloon catheter according to claim 11, wherein a plurality of the convex portions project outwardly from the outer circumferential surface of the second layer and are circumferentially spaced apart from one another, and wherein a plurality of the concave portions are provided on the inner circumferential surface of the first layer and are circumferentially spaced apart from one another, each of the convex portions being positioned in one of the concave portions, the plurality of the convex portions being equal in total number to the total number of the concave portions.

17. The balloon catheter according to claim 11, wherein a plurality of the convex portions project outwardly from the outer circumferential surface of the second layer and are circumferentially spaced apart from one another by a circumferential spacing, the circumferential spacing between at least a first and a second immediately circumferentially adjacent convex portions being different.

* * * * *